US012642962B1

(12) United States Patent (10) Patent No.: US 12,642,962 B1

Reed et al. (45) Date of Patent: Jun. 2, 2026

(54) ELECTRO-STIMULATION PATCH

(71) Applicants: George Ashford Reed, Lake Oswego, OR (US); Patrick Flynn Boileau, Cornelius, OR (US); Wessam Mohamed, Zagazig (EG)

(72) Inventors: George Ashford Reed, Lake Oswego, OR (US); Patrick Flynn Boileau, Cornelius, OR (US); Wessam Mohamed, Zagazig (EG)

( * ) Notice: Subject to any disclaimer, the term of this patent is extended or adjusted under 35 U.S.C. 154(b) by 0 days.

(21) Appl. No.: 19/390,327

(22) Filed: Nov. 14, 2025

(51) Int. Cl.
A61N 1/36 (2006.01)
A61N 1/04 (2006.01)

(52) U.S. Cl.
CPC ....... A61N 1/36014 (2013.01); A61N 1/0496 (2013.01); A61N 1/36034 (2017.08)

(58) Field of Classification Search
CPC .............. A61N 1/36014; A61N 1/0496; A61N 1/36034
See application file for complete search history.

(56) References Cited

U.S. PATENT DOCUMENTS

| | | | |
|---|---|---|---|
| 7,104,965 B1 * | 9/2006 | Jiang ........................ | A61B 5/05 607/116 |
| 2010/0325611 A1 * | 12/2010 | Hudson, III .............. | G06F 8/47 717/110 |
| 2017/0080207 A1 * | 3/2017 | Perez .................... | A61F 5/0003 |
| 2021/0138232 A1 * | 5/2021 | Paz .................... | A61N 1/36031 |

* cited by examiner

*Primary Examiner* — William J Levicky
*Assistant Examiner* — Joshua Brendon Solomon
(74) *Attorney, Agent, or Firm* — Mark S Hubert

(57) ABSTRACT
A disposable, self-contained electro-stimulation device configured with paired cutaneous electrodes for placement over specific acupuncture and neurostimulation points (such P6) on a patient's wrist, delivering controlled electrical pulses to reduce or prevent nausea and vomiting following surgery or anesthesia. Its advanced circuitry trades boost-converter efficiency for total system energy conservation, optimized for the low-duty-cycle pulse output used in neuromodulation rather than continuous high-power operation. Its single-IC, digitally controlled pulse engine performs both biphasic stimulation and contact verification, optimizing it for compact, battery-powered wearable medical devices. It also uses a miniature Hall-effect magnetic-field sensor positioned over a planar helical trace that carries the stimulation current, producing a proportional magnetic field detectable by the Hall sensor for the non-invasive current detection and skin-contact verification.

10 Claims, 11 Drawing Sheets

FIG. 10

ELECTRO-STIMULATION PATCH

COPYRIGHT STATEMENT

FIELD OF THE INVENTION

The present invention relates generally to the treatment and prevention of postoperative nausea and vomiting (PONV) as well as motion sickness.

BACKGROUND OF THE INVENTION

Nausea and vomiting are common complications associated with surgery and anesthesia. Postoperative nausea and vomiting (PONV) can delay patient recovery, prolong hospital stays, and increase overall healthcare costs. Similarly, motion sickness whether it be from water, land or air travel have ruined many a trip or vacation. There are two options. Pharmacological intervention by way of antiemetic drugs and electro-acupuncture or transcutaneous nerve stimulation at the P6 (Neiguan) point on the volar surface of the wrist. However, neither are without their drawbacks.

Antiemetic drugs provide an incomplete effectiveness, and users commonly experience side effects, or contraindications. Electrical stimulation commonly found on wristwatch style stimulators, while efficiently eliminating nausea without the systemic side effects of drugs, because of their cost, are designed to be reusable, and require gels, straps, or separate accessories thus limiting their suitability for use.

There is a need for a low cost, over-the-counter disposable device for the relief of PONV for postoperative use in hospitals or surgical centers and for the prevention and relief of travel sickness. The present invention utilizes new and known technologies to present a novel device for the treatment and prevention of postoperative nausea and vomiting (PONV) as well as motion sickness.

BRIEF SUMMARY

A disposable, self-contained electro-stimulation device configured with paired cutaneous electrodes for placement over specific acupuncture and neurostimulation points (such P6) on a patient's wrist, delivering controlled electrical pulses to reduce or prevent nausea and vomiting following surgery or anesthesia.

A single patient, disposable battery powered adhesive patch that provides reliable stimulation to relieve nausea when its pair of electrodes are positioned over the P6 acupuncture point, and that incorporates built-in safety and usability features including skin contact detection, low battery shut off, and LED indicators.

A disposable electro-stimulation device designed for application to a patient's wrist, that reduces or prevents postoperative or motion sickness nausea and vomiting.

A battery powered electronic anti-nausea patch that trades boost-converter efficiency for total system energy conservation, optimized for the low-duty-cycle pulse output used in neuromodulation rather than continuous high-power operation.

A battery powered electronic anti-nausea patch that is a single-IC, digitally controlled pulse engine performing both biphasic stimulation and contact verification, optimizing it for compact, battery-powered wearable medical devices.

A battery powered electronic anti-nausea patch that uses a miniature Hall-effect magnetic-field sensor positioned over a planar helical trace that carries the stimulation current, producing a proportional magnetic field detectable by the Hall sensor for the non-invasive current detection and skin-contact verification.

BRIEF DESCRIPTION OF THE DRAWINGS

Reference is made to the accompanying drawings, in which like reference numerals identify like elements throughout the several views. The drawings illustrate exemplary embodiments of the electro stimulation patch, including the arrangement of the electronics.

Figure 10:
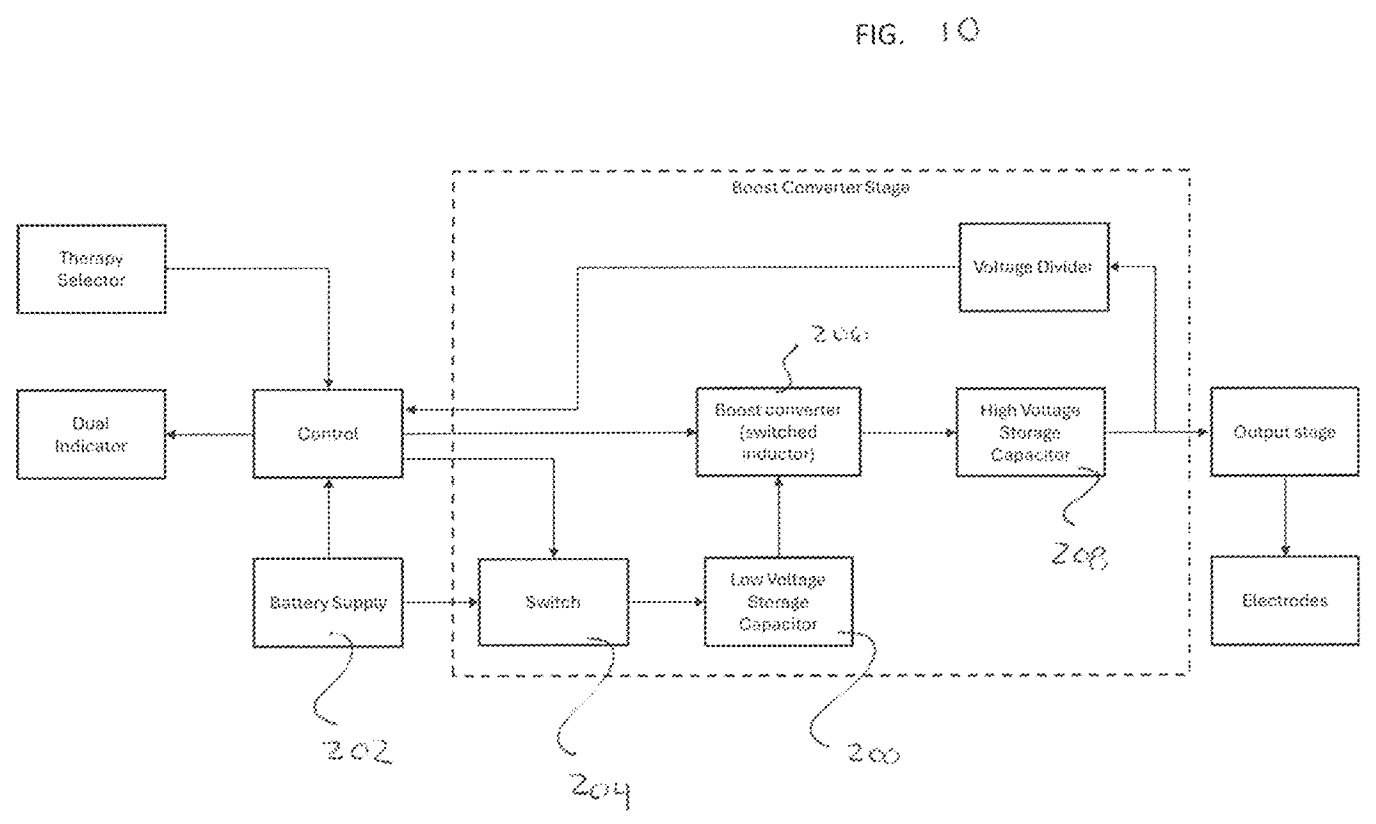

FIG. 10 is a modular representation of the ESP pulse generation and LED feedback logic electronics.

DETAILED DESCRIPTION OF THE INVENTION

Figure 1:
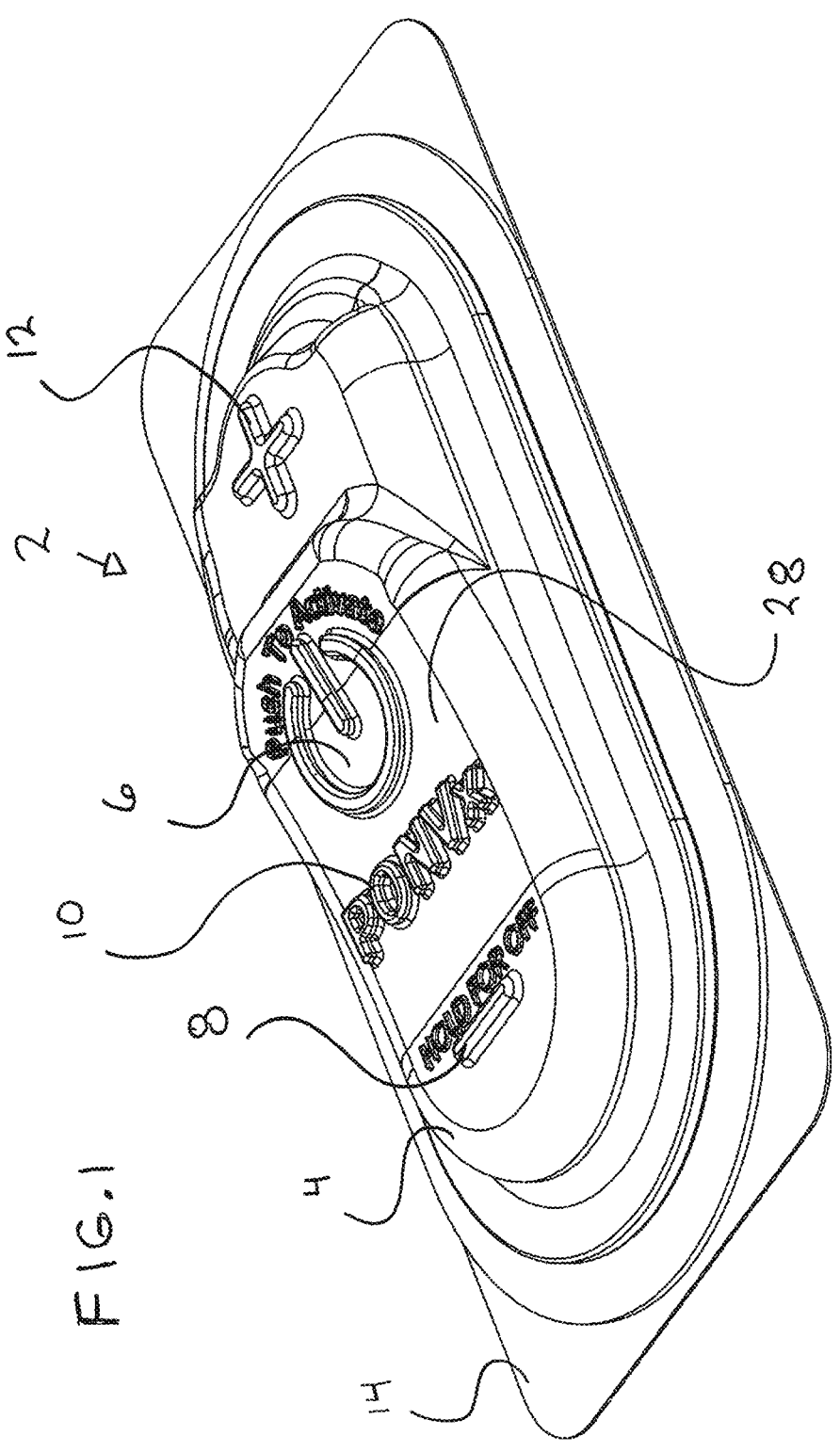
FIG. 1 is a top perspective view of the electro-stimulation patch (ESP)

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details.

It will be understood that, although the terms first, second, etc. may be used herein to describe various elements, these elements should not be limited by these terms. These terms are only used to distinguish one element from another. For example, a first attachment could be termed a second attachment, and, similarly, a second attachment could be termed a first attachment, without departing from the scope of the inventive concept.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes all combinations of one or more of the associated listed items.

The terminology used in the description of the inventive concept herein is for the purpose of describing embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The present invention is a self-contained, battery powered, disposable, flexible, oval electro-stimulation patch (ESP) designed for application to a patient's wrist, with optional placement of a second electrode pad at an alternate acupuncture site such as ST36. The ESP is intended for single-patient use under clinical supervision and is discarded after treatment, thereby eliminating cross-contamination risks and simplifying the post operative workflow. Compared with the prior art, reusable electro-stimulation wristbands, the ESP offers a lower cost, simplified device, that offers enhanced infection control, while maintaining effective stimulation at clinically validated acupuncture points to reduce PONV.

Decades of use of transcutaneous stimulation over the P6 (Neiguan) region of the median nerve have demonstrated benefit for nausea/retching/vomiting across multiple etiologies (motion sickness, pregnancy, chemotherapy) and as an adjunct in reducing postoperative nausea—this is codified repeatedly in numerous of the FDA's ReliefBand® clearances and summaries. Those summaries specify the target site (ventral wrist at P6) and describe wrist-worn devices delivering fixed-frequency, fixed-width, asymmetric biphasic pulses via two skin contacts, with user-selectable intensity levels and battery power, establishing a technological predicate landscape for PONV mitigation by median-nerve stimulation.

ReliefBand® wrist-worn devices have long dominated the market for non-pharmacologic nausea management. Earlier generations (Maven/Woodside) established a wearable form factor with 31 Hz fixed frequency, fixed pulse width, and user-adjustable amplitude through a dial or button interface. The present patch diverges by eliminating the strap and exposed metal contacts, delivering a complete adhesive patch design with embedded electrodes and electronics. Its three layere design consist of a top nonwoven interface, a middle hydrogel-free conductive adhesive film/ transfer tape containing carbon fibers that is corrosion resistant and ensures proper current distribution, and a bottom layer of a biocompatible hydrogel pad that is a hydrophilic material made of a network of polymers. Together the three layer design provides stable impedance, comfort, and corrosion resistance not achievable with direct metal-skin contact of the prior art devices. The ESP introduces a sealed, disposable form factor and new patient interface technology for anti-nausea treatment.

Figure 2:
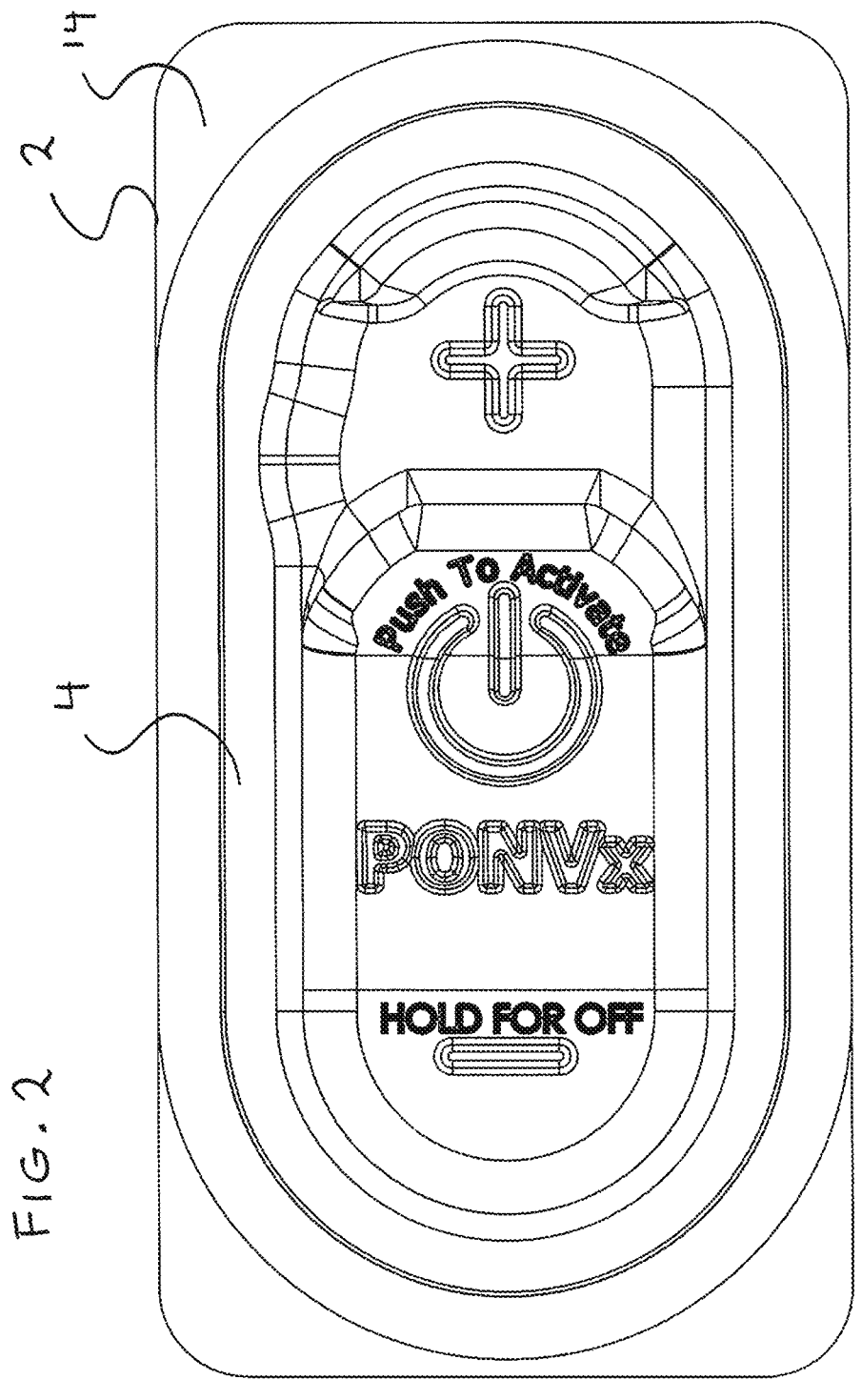
FIG. 2 is a top view of the ESP.
Figure 3:
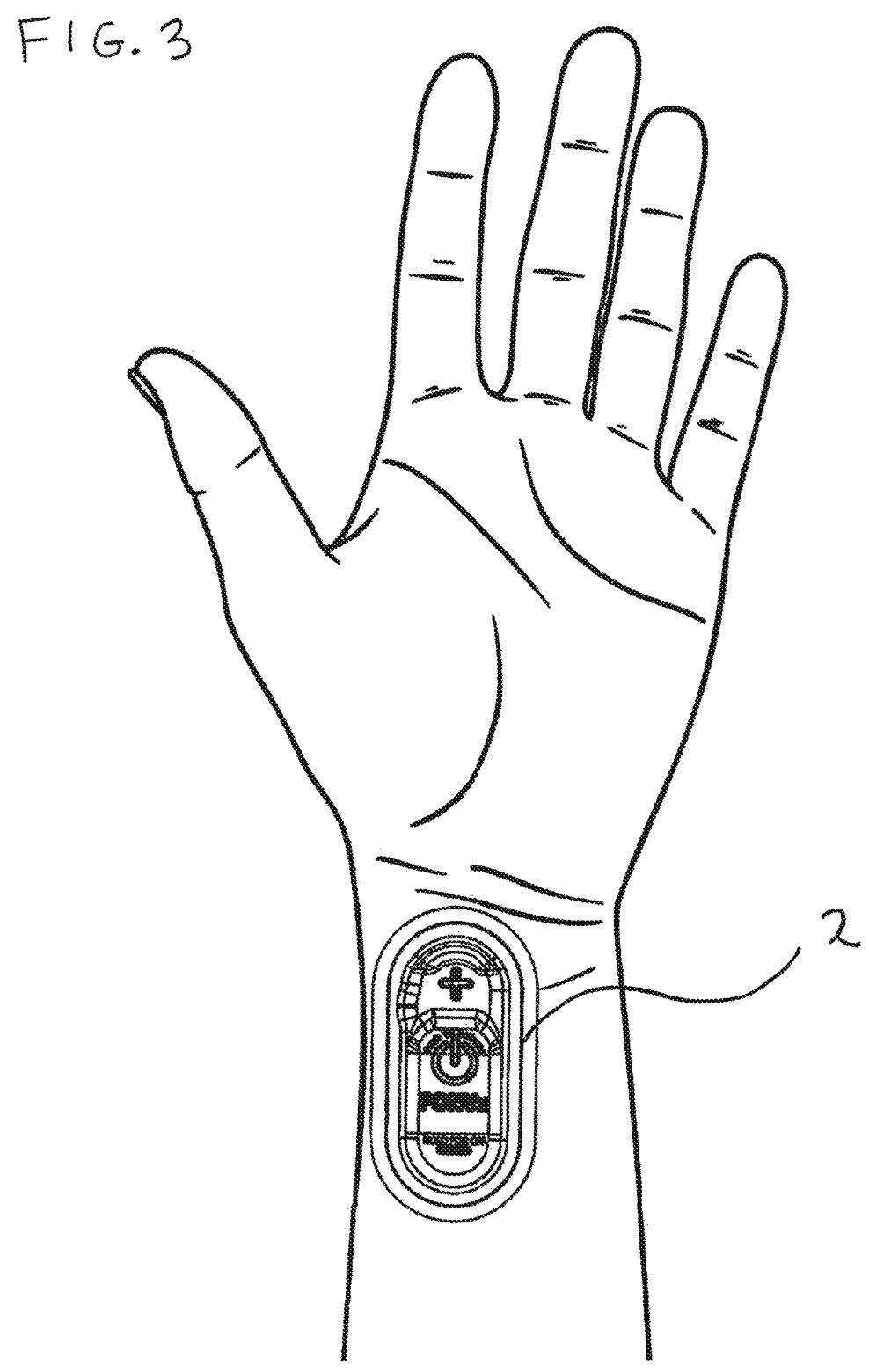
FIG. 3 is a front view of an ESP in use affixed to a patient's arm.
Figure 8:
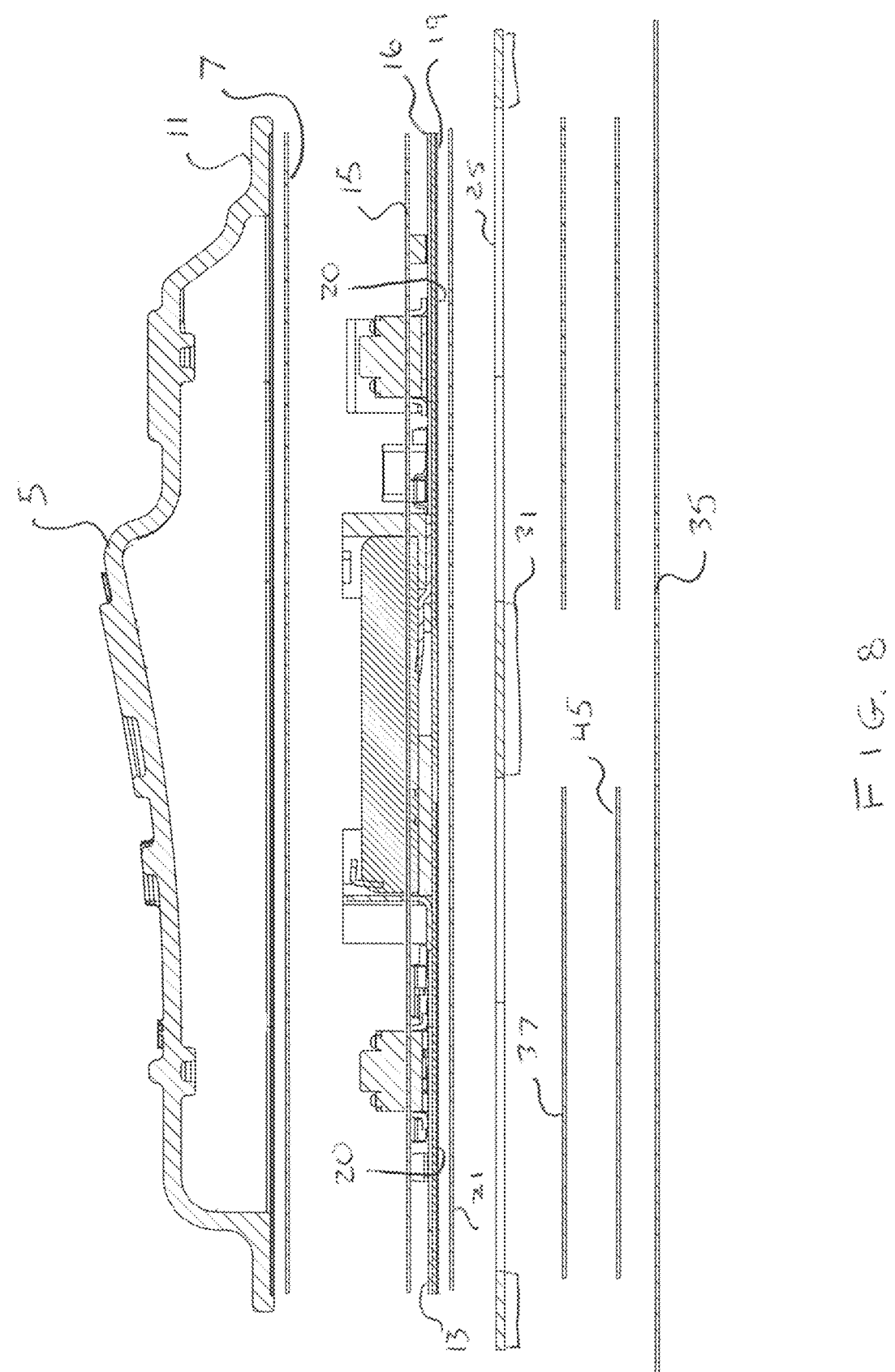
FIG. 8 is side cross sectional exploded view of the ESP.

FIGS. 1 and 2 illustrate perspective front and top views of the assembled ESP 2 showing its flexible silicone body 4 which is closely affixed to the top of a flexible substrate printed circuit board 16 (FIGS. 5 and 6) such that the body's top face 28 allows the tactile operation of the PCB's On tactile button 6, Off tactile button 8, its intensity control button 12, and allows any illumination of the operational LEDS 10 to be seen therethrough. There is a hydrogel pad assembly 14 attached to the bottom face of the PCB that adheres to human skin when its release strip 28 (FIG. 5) is removed. The ESP 2 in its simplest terms is silicon body 4 placed over an electronic control circuit on a PCB 16 (FIG. 5) affixed to an adhesive patch that is adapted to provide microcontroller controlled adjustable pulses of electricity provided by its coin battery 18, to a known receptive site at the wrist of a patient through a pair of electrodes 20 on its bottom face 22, (FIG. 9) passing their pulses through a conductive hydrogel pad assembly 24 (FIG. 8) targeting the P6 acupuncture point on the volar wrist. (FIG. 3)

The ESP 2 is made from the assembly of three separately fabricated components held together in an inseparable fashion to form a single-use, disposable device. The three components are: the body 4 (electronics cover), PBC 16 (electronics), and the hydrogel pad assembly 24.

Figure 4:
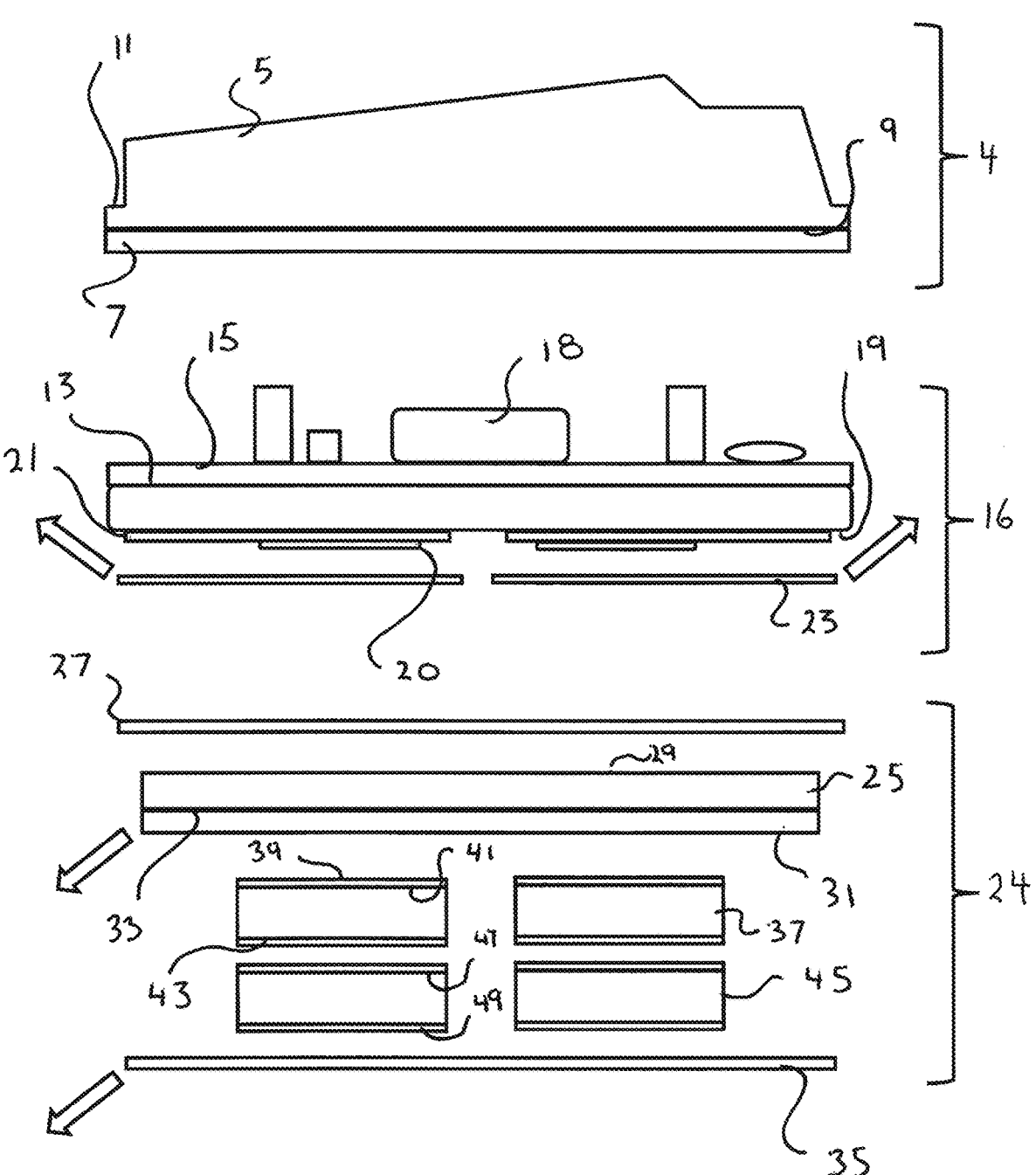
FIG. 4 is a representative side exploded view of the ESP showing all components and adhesives.
Figure 6:
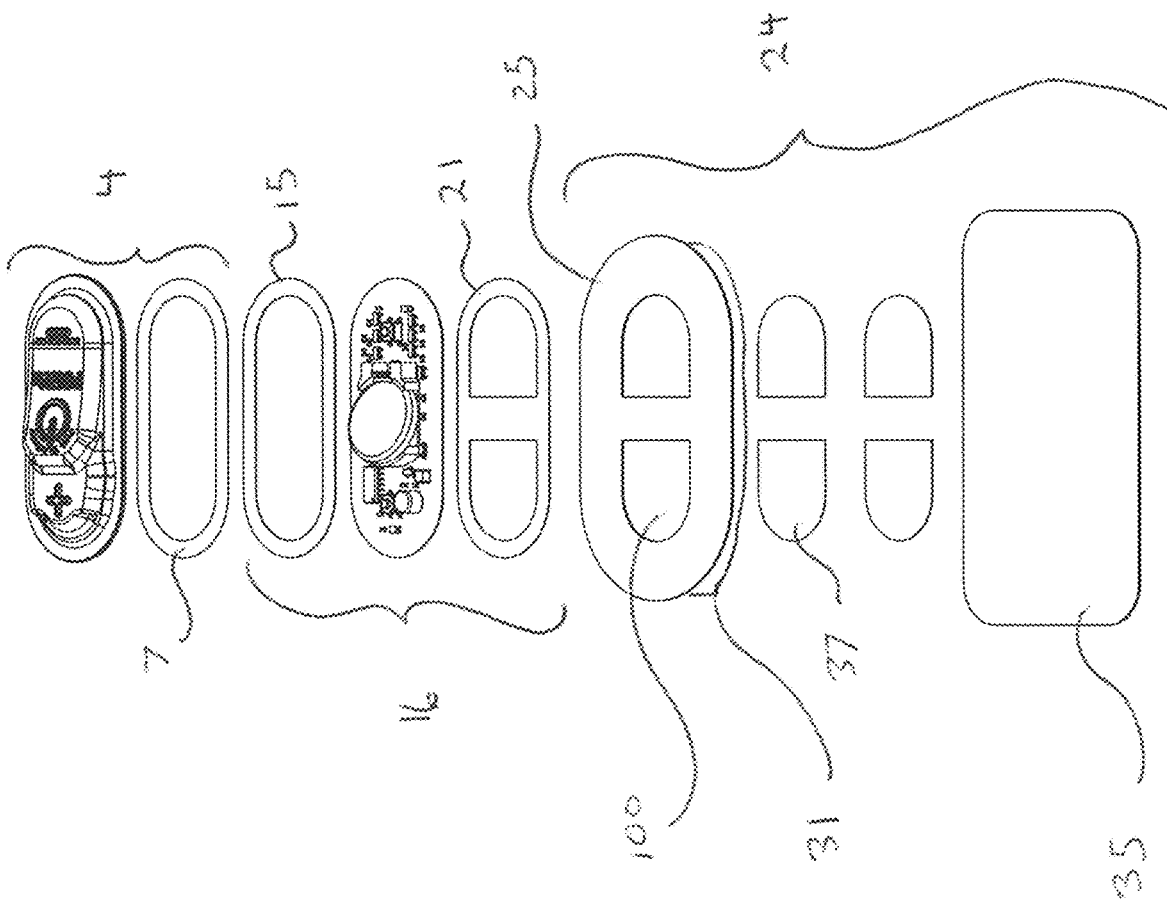
FIG. 6 is a side perspective exploded view of an assembled ESP (with the first guard strip removed)
Figure 9:
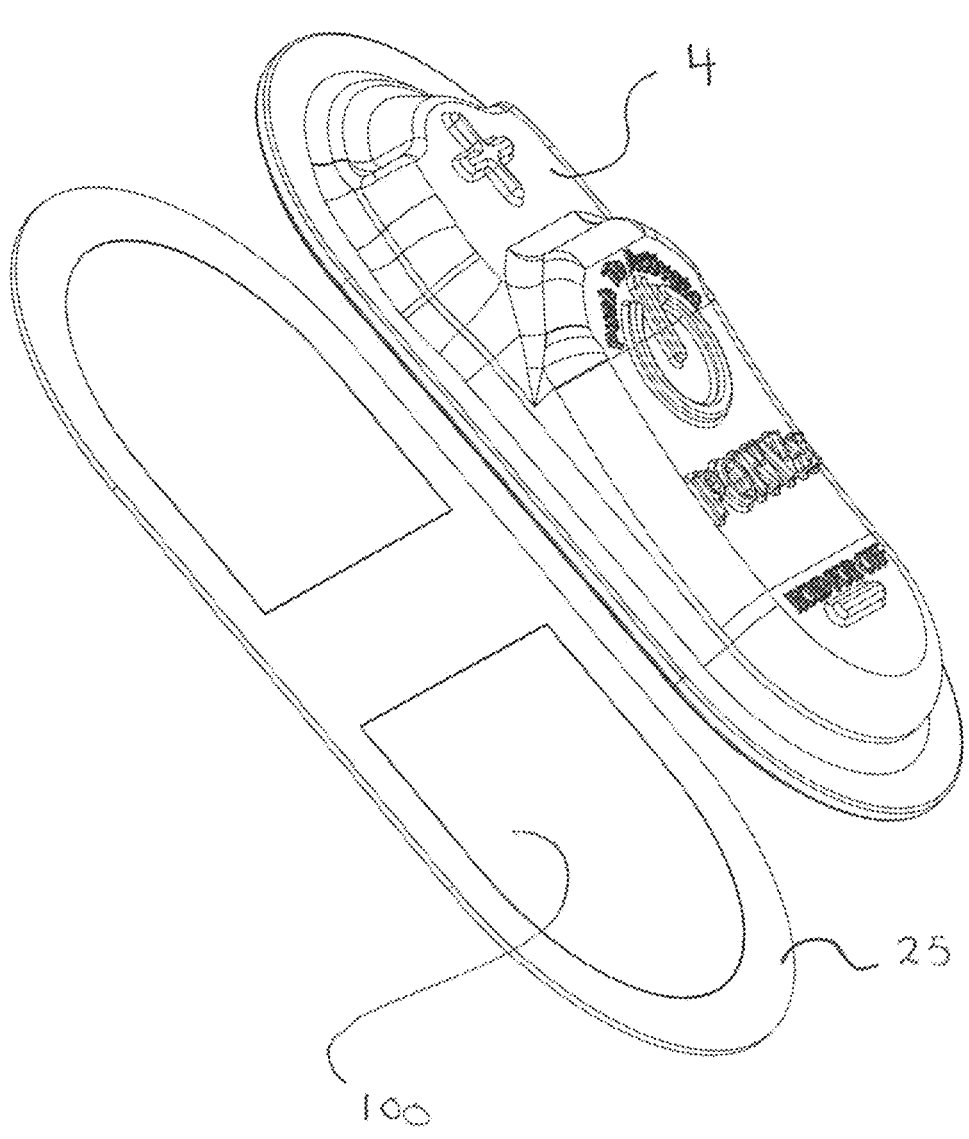
FIG. 9 is a front perspective view of the ESP body and adhesive ring.

FIGS. 4, 6 and 9 best illustrate this layered assembly of the patch 2 from its three components, the body 4 (electronics cover), PBC 16 (electronics), and the hydrogel pad assembly 24. The body 4 is a silicon based translucent, pliable cover 5 that fits atop the PCB 16. The body 4 has a first part contact adhesive 7 about the perimeter of its bottom face 9 of its flange 11.

The PCB 16 is a printed circuit board with the necessary electronics, LEDs and power supply 18 mounted thereon. On the perimeter of its top face 13 there is a second part contact adhesive 15 affixed that matingly engages with the first part contact adhesive 7 to irreversibly mate the body 4 and the PCB 16 together. On the bottom face 19 of the PCB 16 there is a pair of spatially separated electrodes 20, each surrounded by a ring of adhesive 21. There is a first removeable guard strip 23 covering the entire bottom face 19 of the PCB 16 that is removed before the joined body 4 and PBC 16 are affixed to the hydrogel pad assembly 24.

The hydrogel pad assembly 24 is a sandwich of various planar components. It has a non-woven fabric retaining ring 25 with two interior cutouts 100 that the electrodes 20 reside in upon assembly. The retaining ring 25 has a second removeable guard sheet 27 on its top face 29 that when removed along with the first removable guard sheet 23, will allow the first two rings of adhesive 21 to fix the PCB 16 to the retaining ring 25. There is an adhesive 31 on the bottom face 33 of the retaining ring 25 that surrounds both interior cutouts 100 as well as the exterior perimeter of the retaining ring 25. This adhesive 31 bonds to the third removeable guard strip 35 (which is attached to and peeled away before affixing the patch 2 to a patient). This adhesive 31 also bonds to the peripheral edges of the two Hydrogel pads 37. The hydrogel pads are soft, water-rich material made of a network of polymers that can absorb and retain large amounts of water while still holding their shape. The two adhesive film/transfer tape 37 have a matching profile with the interior cutouts 100, that are dimensionally larger, such that the electrodes 20 are fully covered by these pads 37 and their outer edges are affixed to the adhesive 31 on the bottom face of the retaining ring 25. The adhesive film/transfer tape pads 37 have a thin layer of adhesive 39 on their entire top face 41 and bottom face 43. Below the adhesive film/transfer tape pads 37 are the hydrogel pads 45 which share the same dimensions as the adhesive film/transfer tape pads 37 and have a surface adhesive 39 on their top face 47 and bottom face 49. The adhesive film/transfer tape pads 37 and the hydrogel pads 45 have their opposing surfaces adhered together. The third removeable guard strip 35 is also removably affixed to the adhesive 39 on the bottom face 49 of the hydrogel 45 as well as the adhesive 31 on the bottom face of the retaining ring 25. This third removeable guard strip 35 integrated onto the hydrogel pad assembly 24 prevents the hydrogel surface from adhering to packaging and removal for placement on the patient.

When the protective sheet 48 is peeled off the hydrogel pad assembly 24 the bottom face 22 of the PCB 16 can be adhered to the top face of the non-woven fabric polymer retaining ring 25 to join the body 4 and PCB 16 to the hydro gel pad assembly 24.

Discussing the three components in detail, the body 4 is a thin, flexible, translucent silicone cover 5 that matingly conforms to the shape of the underlying PCB 16 and its contained electronics. (FIG. 1) It has visual indications of what PCB controls lie underneath the markings. These include tactile depressible or capacitive regions for on/off 6/8, pulse intensity 12, and a LED region 10 to indicate power is on, whether skin contact is still intact, if voltage is still sufficient, and what level of intensity has been set. Although in the preferred embodiment the body 4 is made of a soft biocompatible polymer (such as such as silicone TPU or EVA) to conform comfortably to the wrist and facilitate adhesion, there are numerous other flexible translucent polymers that are functional and operable equivalents. Once it has been mated to the PCB by the joining of the first and second part contact adhesives 7 and 15, it is intended to be waterproof and never to be disassembled in its lifetime.

The PCB 16 is a planar non-conductive substrate that has all the device's electronics and battery 18 operatively mounted thereon. The bottom face 22 of the PCB 16 has a pair of separated electrodes 20 embedded thereon, and a ring of adhesive 21 about its perimeter and between the electrodes 20. The electrodes 20 are separated by approximately 10 mm and aligned such that when affixed to the volar surface of the wrist, they overlie the P6 (Neiguan) acupuncture point. The electrodes 20 are conductive foil or plated pads, that will be exposed to the Hydrogel pads 37.

Figure 5:
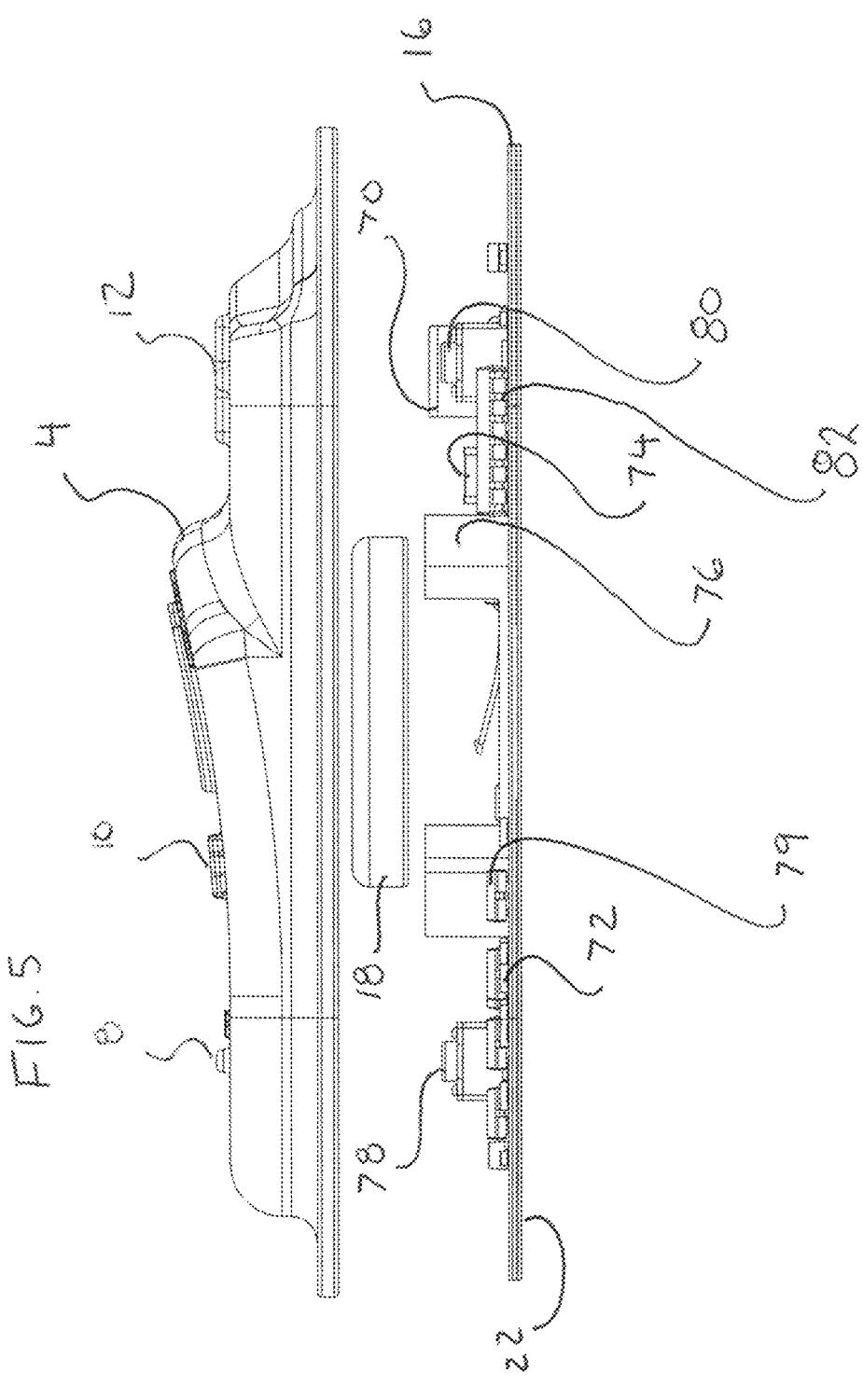
FIG. 5 is a side exploded view of an ESP's body and PCB.
Figure 7:
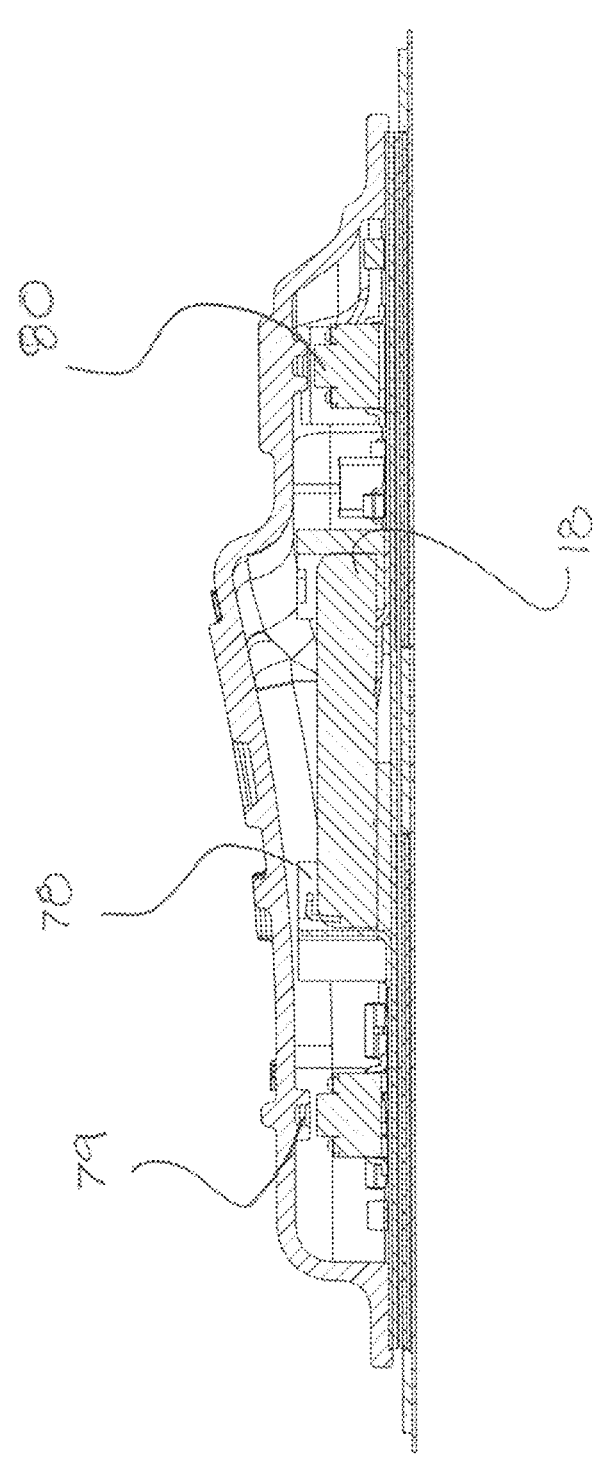
FIG. 7 is a side cross sectional view of an assembled ESP.

Looking at FIGS. 5 and 7, the thin printed circuit board (PCB) 16 has a microcontroller 70 programmed to generate biphasic stimulation pulses, power regulation circuitry 72 and a compact coin-cell battery 18 (e.g., CR2032 format). The microcontroller 70 has an operational circuit that continuously monitors battery voltage and skin contact. If voltage falls below a preset threshold (e.g., 2.0-3.0 V), the patch 2 suspends stimulation and enters standby, and if no skin contact is detected, stimulation ceases and LED visual indication is provided. There is a boost converter 74 and transformer 76 to elevate battery voltage to therapeutic levels, tactile input pads for on/off control 78, and for intensity control 80. LED 79 indicators are operably connected to provide status and feedback through its integrated control circuitry 82.

The PCB's generation of biphasic electrical pulses is accomplished with a programmable stimulation protocol that delivers pulses at defined width and frequency (e.g., ~350 μs at ~31 Hz), with multiple selectable intensity levels. The tactile controls 78, 80 are capacitive touch or button controls for increasing or decreasing intensity, with long-press shut-off. The LED 79 provides user feedback for power-on, intensity level, active operation, low battery, skin contact loss, and power-off sequences. Integrated safety features include a standby mode on loss of skin contact, an automatic shutdown under low battery conditions, and a controlled current output to prevent excessive stimulation.

The control circuit 82 of the patch 2 generates stimulation pulses characterized by a pulse frequency of approximately 31 Hz with a pulse width of approximately 350 microseconds. It applies a biphasic alternating output across the two electrodes 20 and can provide five discrete intensity levels, each increasing amplitude/current.

The hydrogel assembly 24 is best seen in FIGS. 4, 6 and 9. It is a layered sandwich of flexible planar sheets to enable conductivity from the electrodes 20 to the patient without corrosion to the electrodes 20 and while maintaining excellent sealed contact with the patient's skin. There are five sheets in all, the middle three are functional while the top and bottom sheets are releasable, used to expose adhesive on the outer faces of the outer sheets for adhesion to the PCB 16 and the patient's skin.

The top sheet of the hydrogel assembly 24 is a removeable polymer protective sheet 48 with a pull tab to initiate the release. It covers and protects the non-conductive retaining ring 25, which is a non-woven polymer sheet with dual cutouts 100 for the electrodes 20. It ensures proper current distribution. On its bottom face 33 around its perimeter and between its cutouts 100 there is an adhesive 31 used to affix the two underlying hydrogel pads 37 to its bottom face 33. The hydrogel pads 37 conform to the configuration of the cutouts 100 in the retention ring 25 but are dimensionally larger such that they overlap the perimeter of the cutouts 100. The electrodes 20 overlie and contact the hydrogel pads 37 which provide an impedance matching interface and ensure consistent electrical coupling to the skin.

The hydrogel pads 45 have adhesive on both their top face 47 and bottom face 49. Above the hydrogel pads 45 are the two adhesive film/transfer tape pads 37 which are the same size and shape as the hydrogel pads 45. The adhesive film/transfer tape pads 37 are used to protect the electrodes 20 and underlying copper surfaces of the PCB 16 from corrosion caused by hydrogel.

Below the hydrogel pads 45 there is another removeable polymer protective sheet 35 that is removed to allow the retention ring 25 to adhere to the skin. Together the device 2 forms a low-profile patch. This unique sandwich structure is configured to maintain skin adhesion and electrical impedance within a therapeutic range for at least 24 hours of continuous wear.

While prior art devices rely on bare metal contacts, they face variability in skin impedance, corrosion, and patient discomfort. The interface at the adhesive film/transfer tape pads 37 integrate an ionic gel pad laminated to a nonwoven retaining ring that stabilizes contact pressure and distributes current evenly. This structure buffers moisture, maintains impedance stability, and acts as a corrosion barrier. It represents a novel feature differentiating the parch 2 from prior wrist-worn devices. The patch design supports consistent therapeutic output and comfortable multi-hour wear under variable postoperative conditions.

In operation, the third removeable polymer protective sheet 35 is removed and the device is applied to the patient's wrist so that the electrodes 20 contact the skin at the P6 location. The user powers on the device and selects an appropriate stimulation intensity. Electrical pulses are then delivered transcutaneously to the underlying nerve pathway. Stimulation continues until the patch is powered off or removed it from the patient. After use, the patch is discarded.

For FDA regulation, primarily based on the prior art wrist bands, the patch 2 will operate in a technological envelope above or below the following electronic parameters: pulse generation fixed ~31 Hz frequency, fixed pulse width of 350 μs pulse width per phase, five discrete intensity levels (8-40 mA peak), PWM-controlled boost for per-level adjustment, nominal constant-current regulation (±10%), and charge per pulse around 3.1 μC at 500. The output is biphasic pulses alternating polarity. Skin contact detection must occur before stimulation. There is a low-battery cutoff at approximately 3.0 V. The power source is a single CR2032 coin cell expected to last more than 24 hours constant operation. The electrical envelope is ≤6 mA RMS; ≤40 mA peak; compliance voltage sufficient across 1 kΩ.

The patch 2 is designed for use in a clinical postoperative environment. Placement is guided by printed markings aligning with the P6 site. LED 29 behavior provides feedback including, on/off confirmation, intensity level, low-battery, and skin-contact loss indication. The single-use disposable design eliminates reprocessing and cross-contamination risk, simplifying hospital workflow. The patch 2 defaults to standby mode when powered on, requiring the user to select an intensity level before pulses are delivered.

The user interface and controls provide: two control inputs—an increase button (or touch pad) which increments the stimulation intensity by one level, up to the maximum of five and a decrease button (or touch pad) which decrements the intensity by one level; and a long press power on/off the device off and returns it to standby.

The LED visual feedback integrates five LEDs, each corresponding to one intensity level. The LED behavior communicates the following patch states:

Power-on sequence: LEDs illuminate sequentially, hold for one second, then extinguish sequentially.

Intensity check: pressing a button briefly illuminates LEDs up to the current level. Level change: LEDs blink the previous level, then blink the new level.

Low battery: center LED blinks for one second every three seconds.

Skin not detected: center LED blinks for two seconds every five seconds.

Device active: center LED blinks for one second every 0.5 seconds for up to three minutes.

Power-off sequence: all LEDs illuminate for one second, then extinguish sequentially (5-4-3-2-1).

The microcontroller provides the following safety and operating features by continuously monitoring:

Battery voltage: If voltage falls below a preset threshold (e.g., 2.0-3.0 V), the patch suspends stimulation and enters standby.

Skin contact: If no skin contact is detected, stimulation ceases and a visual indication is provided.

Long-press shutoff: A prolonged press of the "decrease" input disables the patch, preventing unintended operation.

Figure 11:
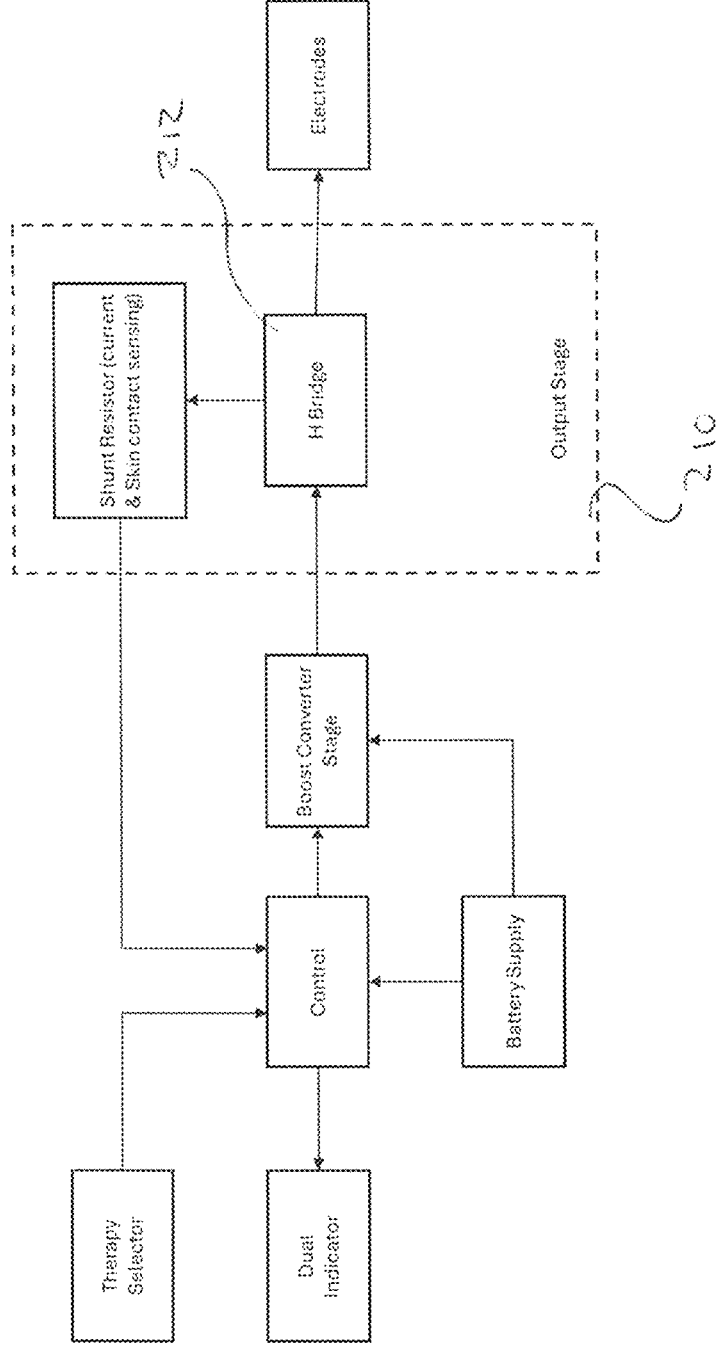
FIG. 11 is a modular representation of the ESP control circuitry and functional components.

There are three improvements in the operating circuit design over the prior art bands. The first (FIG. 11) provides battery life optimization via controlled capacitor isolation the architecture of which introduces a parallel storage capacitor 200 to the lithium coin cell 202 but uniquely interposes an electronic switch 204 between the battery 202 and the circuit (low voltage reservoir capacitor+Boost Converter circuit). During startup, the boost converter 206 typically draws a large inrush current, reducing overall efficiency and shortening battery life. In this design, a microcontroller-controlled switch 204 momentarily disconnects the battery 202 from the circuit during the high-current startup period of the boost phase. The charged reservoir capacitor 208 then acts as a power source. Once the converter circuit stabilizes, the switch 204 reconnects the battery 202 for normal operation and reservoir 208 recharge.

The circuit includes a capacitor 200 connected in parallel with the battery 202 and a transistor (or equivalent electronic switch 204) placed in series with the battery's positive terminal.

The primary purpose of this capacitor 200 is to absorb and supply transient current during the initial boost or inductor energizing phase, thereby shielding the battery 202 from sudden current spikes or voltage reversals. When the boost converter 206 or inductor is activated, the isolation transistor temporarily opens 204 (disconnects the battery 202). During this brief interval, the parallel capacitor 206 provides the instantaneous current needed for the inductor 206 charging pulse. This arrangement effectively prevents high di/dt stress, voltage spikes, and reverse energy injection into the battery 202 that typically occur during boost startup. Once the inductor current stabilizes, the transistor 204 reconnects the battery 202, allowing normal operation and supply replenishment of the capacitor 200.

The result is a compact, low-loss battery protection and dynamic energy buffering system that increases cell lifespan and improves the stability of high-voltage pulse generation circuits powered by small cells (e.g., coin cell batteries).

This approach intentionally trades boost-converter efficiency for total system energy conservation, optimized for the low-duty-cycle pulse output used in neuromodulation rather than continuous high-power operation. The circuit thereby extends battery life without affecting therapeutic output consistency. This selective capacitor isolation for controlled current draw has not been observed in prior art band devices.

The second improvement in the operating circuit design is an output stage integration that uses a high-voltage H-bridge integrated circuit 210. (FIG. 11) Here the current output driver consists of eight discrete transistors and eight corresponding resistors forming complementary half-bridges that produce alternating polarity pulses across the patient electrodes. The proposed improvement substitutes this discrete network with a single integrated H-bridge driver IC 212 rated for at least 40 V operation.

This substitution would: consolidate 16 passive and active components into one IC package; simplify PCB routing, reduce parasitic imbalance, and improve manufacturing reliability; and provide symmetrical switching control for biphasic pulse generation.

The technical challenge was in sourcing an H-bridge driver with sufficient voltage headroom (≥40 V) to match the compliance range used in current stimulation. Additionally, the integrated topology complicated current-sense feedback as the discrete resistors currently enable measurement of electrode current and skin impedance. This is resolved by placing a shunt resistor (low value) between the H bridge IC and ground by which the returning current from skin is sensed. This will enable skin detection and current optimization along with better safety. Simplified biphasic pulse generation using integrated H-bridge IC and shunt-based contact sensing The patch employs a commercially available H-bridge driver IC, originally designed for driving brushed DC motors, as a compact biphasic pulse generator. This replaces the traditional discrete transistor H-bridge topology (typically 8 or more discrete BJTs or MOSFETs with driver stages), thereby significantly reducing component count, PCB area, cost, and assembly complexity. This integrated H-bridge IC provides matched, protected half-bridge outputs capable of polarity reversal, enabling precise generation of biphasic stimulation pulses from a low-voltage control signal.

A low-value shunt resistor is placed at the ground return path of the H-bridge IC, allowing direct measurement of the instantaneous current delivered to the load. The microcontroller senses the voltage across the shunt to monitor pulse current amplitude for closed-loop control and safety; and detect electrode contact by identifying open-circuit conditions (zero or near-zero current) before each stimulation cycle.

This dual-purpose sensing eliminates the need for separate contact-detection circuits or high-impedance sensing networks, further reducing the components.

This approach transforms a conventional multi-transistor analog design into a single-IC, digitally controlled pulse engine that performs both biphasic stimulation and contact verification, making it ideal for compact, battery-powered medical or wearable systems.

The third improvement in the operating circuit design is a patient-current and skin-contact sensing via Hall-Effect field detection. (FIG. 12) Current measurement and skin detection are essential for patient safety and therapy verification. The design of prior art wrist devices relies on a shunt resistor placed on the return (ground) path to measure current flow and detect electrode contact through pulse-return sensing. Although functional, the resistor consumes power continuously and introduces voltage drop losses. The improvement in the patch replaces or supplements the shunt resistor with a miniature Hall-effect magnetic-field sensor positioned over a planar helical trace on a multilayer PCB. The helix carries the stimulation current, producing a proportional magnetic field detectable by the Hall sensor. This configuration enables non-invasive current detection and skin-contact verification while eliminating most of dissipative losses inherent to resistive sensing.

When a 40 V test pulse is emitted toward the patient, the returning current generates a detectable field through the PCB helix. The Hall sensor output confirms both the presence of a conductive skin path and the amplitude of the delivered current, allowing the microcontroller to validate electrode contact before therapy delivery; detect over-current conditions in highly conductive skin (e.g., pediatric patients); and ensure stimulation current remains within defined milliampere safety limits This low-loss magnetic current-sensing scheme provides dual functionality-skin detection and current safety monitoring-in a single solid-state component with negligible power consumption, potentially enhancing both energy efficiency and patient protection.

Thus the patch provides the following three functional advantages over the prior art: switched capacitor isolation that reduces startup current draw, extends coin cell battery life; a single-IC H-bridge output that allows component reduction and a balanced biphasic drive without discrete transistor networks for output pulse control; and a Hall-effect current and skin detection allowing low dissipation sensing and magnetic feedback of the return current.

While certain features and aspects have been described with respect to exemplary embodiments, one skilled in the art will recognize that numerous modifications are possible. Moreover, while the procedures of the methods and processes for building, assembling and using the devices described herein are described in a particular order for ease of description, unless the context dictates otherwise, various procedures may be reordered, added, and/or omitted in accordance with various embodiments. What is claimed as the invention, therefore, is all such modifications as may come within the scope and spirit of the following claims and equivalents thereto.

Having thus described the invention, what is claimed as new and desired to be secured by Letters Patent is as follows:

1. An electro-stimulation patch for reducing or preventing nausea and vomiting, by affixation at a patient's acupuncture or neurostimulation site, comprising:

a printed circuit board (PCB) comprising a battery and a battery powered control circuit with a microcontroller that generates biphasic stimulation pulses at a predetermined frequency and a pulse width, presented through a pair of electrodes exposed on a bottom face of said PCB;

a flexible, adhesive body residing atop of and permanently adhered about a perimeter of said PCB, adapted to seal and protect said PCB while allowing tactile control to an underlying set of on/off and intensity level functions of said control circuit;

a layered pad assembly adhered to a bottom face of said PCB and serving as an interface between said pair of electrodes and said patient, said pad layers comprising a non-conductive retention ring having openings aligned with said electrodes, a twin hydrogel-free conductive adhesive film/transfer tape containing carbon fibers beneath said electrodes that ensures proper current distribution, electrical impedance stability and conductive coupling between said electrodes and said patient, a twin hydrogel pad layer beneath said transfer tape that is a biocompatible hydrophillic material made of a network of polymers that provides stable impedance, comfort, and corrosion resistance for minimization of corrosion of said electrodes from patient's skin, a plurality of adhesive layers to bind together the layered pad assembly, and a removable bottom protective sheet.

2. The electro-stimulation patch of claim 1, wherein said body is composed of a translucent, biocompatible polymer selected from the group consisting of silicone, thermoplastic polyurethane (TPU), or ethylene-vinyl acetate (EVA).

3. The electro-stimulation patch of claim 2, further comprising LEDs visible through said translucent body, said LEDs configured to communicate operational states of said control circuit including said on/off, said intensity level, a low-battery condition, and a loss of skin-contact condition.

4. The electro-stimulation patch of claim 1, wherein the adhesive body, PCB, and hydrogel pad assembly are permanently bonded to form a single-use, waterproof, disposable unit.

5. The electro-stimulation patch of claim 1, wherein the stimulation pulses are generated at approximately 31 Hz and have a 350 microsecond pulse width per phase.

6. The electro-stimulation patch of claim 1, wherein said microcontroller has an operational circuit that continuously monitors battery voltage and skin contact, providing LED illumination, suspending ESP stimulation and putting said ESP in a standby mode if voltage falls below a preset threshold and if no skin contact is detected, and resumes operation upon restoration of acceptable conditions.

7. The electro-stimulation patch of claim 1, wherein said battery is connected to a parallel storage capacitor through a microcontroller-controlled isolation switch configured to disconnect the battery during high-current startup events to protect the battery and extend its life.

8. The electro-stimulation patch of claim 1 further comprising a Hall-effect sensor disposed proximate a current-carrying trace on a printed circuit board, said Hall-effect sensor detecting a magnetic field produced by a planar helical trace carrying said stimulation current monitoring ESP stimulation current to determine electrode contact integrity.

9. The electro-stimulation patch of claim 1, further comprising a H-bridge driver integrated circuit, thereby reducing component count and providing balanced polarity switching for said biphasic stimulation pulses.

10. A method for reducing postoperative or motion-induced nausea and vomiting, comprising:

applying an electro-stimulation patch according to claim 1 to a patient's wrist over a P6 acupuncture point;

activating the patch to generate biphasic electrical pulses between the pair of electrodes through the patient's skin;

suspending stimulation in response to loss of skin contact or low battery voltage; and continuing stimulation until the patch is manually turned off or removed.

\* \* \* \* \*